(12) United States Patent
Foster

(10) Patent No.: US 10,803,772 B1
(45) Date of Patent: *Oct. 13, 2020

(54) SURGICAL IMPLEMENT TRAINING PROCESS

(71) Applicant: SMITH & NEPHEW ORTHOPAEDICS AG, Zug (CH)

(72) Inventor: Larry Foster, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 221 days.

This patent is subject to a terminal disclaimer.

(21) Appl. No.: 15/905,355

(22) Filed: Feb. 26, 2018

Related U.S. Application Data

(63) Continuation of application No. 15/223,727, filed on Jul. 29, 2016, now abandoned, which is a continuation of application No. 13/338,900, filed on Dec. 28, 2011, now Pat. No. 9,847,044.

(60) Provisional application No. 61/429,369, filed on Jan. 3, 2011.

(51) Int. Cl.
    *G09B 23/28* (2006.01)
    *G09B 5/06* (2006.01)

(52) U.S. Cl.
    CPC .............. *G09B 23/28* (2013.01); *G09B 5/065* (2013.01)

(58) Field of Classification Search
    CPC ....................................................... G09B 23/28
    USPC .......................................................... 434/262
    See application file for complete search history.

(56) References Cited

U.S. PATENT DOCUMENTS

2006/0040245 A1* 2/2006 Airola ...................... G09B 5/00
    434/262
2006/0142739 A1* 6/2006 DiSilestro .............. A61B 90/90
    606/1

* cited by examiner

*Primary Examiner* — Thomas J Hong
(74) *Attorney, Agent, or Firm* — David Chambers

(57) ABSTRACT

A surgical implement training process that includes teaching an identity of a plurality of first surgical implements in a first surgical implement tray, a location of the plurality of first surgical implements in the first surgical implement tray and an actual order in which each of the first surgical implements are used when performing a surgical procedure. A surgical implement selection system includes a display portion and an input portion. The first surgical implement tray is played on a first display region of the display portion. First images of the first surgical implements in the first display region are selected which causes the first images of the selected first surgical implements to appear in a second display region of the display portion. Each of the first images includes one of the first surgical implements. The first images are organized in the second display region in a testing order based upon when the first surgical implements are used when performing the surgical procedure. It is evaluated whether the testing order matches the actual order.

18 Claims, 9 Drawing Sheets

FIG. 9

PRODUCT TRAINING TEST — 900

Instructor: S2 Interactive
Class: Dr. Johnson - Spine
Tester: Larry Foster

Date: 15-15-2011
Time: 1:30 PM
Elapsed: 23 min
— 918

Multiple Choice: 5 of 6
Multiple Choice Score: 83%
Instrument Order Score: 81%
— 916

OVERALL SCORE 82% — 914

— 912

Part I: Internal Fixation

1) The optimal environment for fractures to heal is
   correct   a. Stable
             b. Shear
             c. Rotation 2) The size of the IM Nail for Femoral Fractures
             a. 7mm
   correct   b. 9mm
             c. 14mm 3) The dimensions of the locking screws for IM nails
             a. 4.5mm
   wrong     b. 5.5mm
             c. 8.5mm 4) The position of the patient for our procedure
             a. Prone
   correct   b. Supine
             c. Lateral with knees flexed
             d. 45 degrees lateral 5) The anatomical starting point for Product ZYZ
   correct   a. Greater Trochanter
             b. Lesser Trochanter
             c. Piriformis Fossa
             d. Anterior Hip Capsule 6) The average blood loss according to JBJS article, Feb. 2010, by Jones et. al.
             a. 50cc
   correct   b. 150cc
             c. 550cc
             d. Minimal

— 910 (×3)

SURGICAL IMPLEMENT TRAINING PROCESS

REFERENCE TO RELATED APPLICATION

This application is a continuation of U.S. patent application Ser. No. 15/223,727 filed Jul. 29, 2016, which is a continuation of U.S. patent application Ser. No. 13/338,900 filed Dec. 28, 2011, now U.S. Pat. No. 9,847,044 granted Dec. 19, 2017, which claims priority to U.S. Provisional Application No. 61/429,369, which was filed on Jan. 3, 2011, the contents of which are incorporated herein by reference.

FIELD OF THE INVENTION

An embodiment of the invention relates to surgical procedures. More particularly, the invention relates to a surgical implement training process.

BACKGROUND OF THE INVENTION

In many hospitals, the operating room plays an important role in the care that is provided to patients. The operating room is generally designed to accommodate multiple surgical specialties and their associated surgical staff and surgical equipment.

While the operating room has the potential to be used to save a patient's life, the risks associated with the operating room are quite high because the patient may suffer serious injury and/or death if aspects of the operating room are not correct. For example, there may be serious health consequences if the designated portion of the operating room is not maintained sterile.

Because of the costs of the equipment used in the operating room and the precautions that must be taken to protect the patient such as from infection, the operating room is very costly. There are also significant costs associated with the persons who perform and/or assist with surgeries.

Most hospitals receive a large portion of their revenue from insurance companies and/or governmental agencies. These organizations will often impose strict guidelines on how much revenue the hospital receives for performing particular procedures. Accordingly, the hospitals must balance patient care with cost concerns.

The space within the operating room is typically quite limited as the operating room may have an area of between about 300 square feet and about 550 square feet. This limited size presents challenges in view of the proliferation of advanced technology that has been introduced for the operating room over the past decade.

Technological developments have resulted in a dramatic increase in the number and complexity of operating room equipment and supplies. This equipment and supplies can lead to clutter in the operating room, which can present a significant challenge to patient safety in the operating room environment.

For example, heavy or large equipment that may be either permanently installed or moved into and out of the operating room during an operation. This equipment can create obstacles to movement of staff and equipment within the operating.

Furthermore, electrical wiring, vacuum tubes, gas hoses and garbage receptacles may be present in the operating room. These items represent serious safety hazards to surgeons, nurses, technicians and patients. Intra-operative complications due to staff injury and equipment dislocation have caused dramatic clinical consequences for patients and liability for both physicians and hospitals.

The lack of real-time information on the patient and the applicable surgical procedures has resulted in an environment that is inefficient. These inefficiencies lead to lost time and hospital errors when critical data is missing and/or inaccessible.

Sharing of patient information, radiology studies, test results, and pathology reports is limited. Despite the technological digital revolution that has taken place in our offices and our homes, operating room information technology has progressed little in the last thirty years.

Surgical device manufacturers produce the surgical devices and distribute the surgical devices with instructions for using the surgical devices. In many countries, the surgical devices and the instructions for using the surgical devices must be approved by a governmental regulatory organization before the surgical devices may be distributed.

For example, in the United States, the Food and Drug Administration is the governmental regulatory organization that reviews surgical devices. Depending on the type of surgical device, the request for approval to distribute medical devices generally falls within either a PMA or a 510k.

Hospitals may require the surgeon to be trained on the procedures associated with the use and/or implantation of the surgical device. This training is typically done by the company that manufactures, distributes and/or imports the surgical device.

In addition to the surgeon, there are typically several other persons present in the operating room while the surgical procedure is being performed. One such person in the operating room is a surgical technologist who has the responsibility of ensuring that the items that will be needed when performing the surgical procedure are provided to the surgeon at the appropriate time and in a sterile environment.

It was previously customary for a surgical technologist to be assigned to a particular surgeon(s). In such situations, the surgical technologist was typically able to become familiar with the surgical procedures that were performed by the surgeon(s) to which he/she was assigned. The surgical technologist thereby gained familiarity with the surgical devices, surgical instruments and other associated items that were used by the assigned surgeon(s) thereby leading to an efficient surgical procedure.

There has been a trend away from assigning surgical technologists to particular surgeons. Rather, the surgical technologists have an assigned work schedule. While the surgical technologist is on-duty, the surgical technologist may participate in a variety of surgical procedures that are performed by a variety of surgeons.

In view of the preceding changes, it may be more challenging for the surgical technologist to gain a high degree of familiarity with the surgical instruments that are used in conjunction with all of the surgical procedures on which the surgical technologist assists.

Another issue that affects the ability of the surgical technologist to become familiar with surgical instruments that are used when performing particular surgical techniques is the fact that there is a high degree of turnover with surgical technologists. Recent data reflects a turnover rate of 14% for surgical technologists (2008 NCHA Workforce Report, April 2009; Sarah J. Broome, PhD. Director of Economic Research, North Carolina Hospital Association)

Some of the most complex surgeries are orthopedic and spine procedures. These procedures may take 2-4 hours to complete and require the use of complex instrument sets. To enhance the ability to handle the complex instrument sets, the instruments may be placed into trays. These comments also apply to implants that are used in conjunction with the surgical procedures.

The instruments may be organized into particular trays based upon the procedure with which the instruments are intended to be used. For example, in total joint surgeries there may be separate trays for femoral and tibial instruments.

In an effort to overcome the surgical technologist not being familiar with the surgical instruments used in a particular procedure, a representative from the manufacturer of the surgical device and/or instrument may be present in the operating room while the surgical procedure is being performed so that the representative could answer questions relating to the selection of the particular surgical devices and/or instruments.

It is desirable to minimize the number of people within the sterile field in the operating room because such additional people may increase the risk of patent infection as well as potentially interfere with the movement of the people in the sterile field performing the surgical procedure or assisting in the surgical procedure.

In view of the preceding comments, it is customary for the surgical device/instrument representative to be outside of the sterile field in the operating room. Because of this position, the representative is not able to directly point at the surgical instrument. Rather, the representative will typically use a pointing device to identify a particular surgical instrument. One such suitable pointing device is a laser pointer that enables the surgical instrument to be identified without placing any objects into the sterile field.

While such a technique ensures that the surgical instruments are promptly and accurately provided to the surgeon, the presence of the surgical device/instrument representative in the operating room represents a significant cost to the surgical device/instrument manufacturer and/or representative and a potential distraction for the surgical team.

In the case where the costs are born by the surgical device/instrument manufacturer, such additional cost must be incorporated into the prices of the surgical devices and/or instruments.

In the case where the costs are born by the representative, the representative loses selling time that may be used for calling on other customers. Such a reduction in promotional activities can lead to a reduction in income for the representative.

In an attempt to overcome the preceding effects on the representative, some representatives hire associates to be present in the operating room during the surgical procedures in which the surgical devices/instruments are used. This associate representative is trained on the surgical instruments and the order in which the surgical instruments are used during particular surgical procedures.

Even though the compensation for the associate representative is generally less than the compensation of the representative, the compensation for the associate representative still is a significant expense that must be paid by the surgical device/instrument manufacturer and/or representative.

As is referenced above, surgical instruments may be provided by the manufacturer in trays based upon the type of surgical procedure the surgical instruments are intended to be used with. While the surgical instruments may be provided by the manufacturer or distributor in a clean configuration, they are generally not provided in a sterile configuration.

Even if the surgical instruments were provided in a sterile configuration, it is the procedure of many hospitals to resterilize the surgical instruments so that the hospital can guarantee the sterility of the surgical instruments when they are used in conjunction with a surgical procedure.

Hospitals have a Central Sterile Supply department that is dedicated to sterilizing surgical instruments. This department may be located within the hospital to minimize the potential of the surgical instruments being exposed to pathogens and/or environmental elements such as rain that could impact the sterility of the surgical instruments.

When the surgical instruments are received in the sterilization department, the surgical instruments are generally removed from the trays in which the surgical instruments are delivered from the manufacturer or distributor. The surgical instruments are then processed through the sterilization process such as by using an autoclave.

Once the surgical instruments are sterilized, the surgical instruments must be reassembled into the correct position in the correct surgical instrument tray. To assist the sterilization staff to correctly reassemble the surgical instruments into correct way and in the correct surgical instrument tray, images of the correctly assembled surgical instrument trays may be displayed in the surgical department.

SUMMARY OF THE INVENTION

An embodiment of the invention is directed to a surgical implement training process. An identity of a plurality of first surgical implements in a first surgical implement tray is taught to a person. A location of the plurality of first surgical implements in the first surgical implement tray is taught to the person. An actual order in which each of the first surgical implements are used when performing a surgical procedure is taught to the person.

A surgical implement selection system comprising a display portion and an input portion is provided to the person. The first surgical implement tray is played on a first display region of the display portion. First images of the first surgical implements are selected in the first display region which causes the first images of the selected first surgical implements to appear in a second display region of the display portion. Each of the first images includes one of the first surgical implements.

The person organizes the first images in the second display region in a testing order based upon when the first surgical implements are used when performing the surgical procedure. It is evaluated whether the testing order matches the actual order.

Another embodiment of the invention is directed to a method of influencing a surgeon to select a source for a surgical implement set that is used in conjunction with a surgical procedure. Training is done by a person who will be assisting a surgeon during a surgical procedure.

An identity of a plurality of first surgical implements in a first surgical implement tray is taught to the person. A location of the plurality of first surgical implements in the first surgical implement tray is taught to the person. An actual order in which each of the first surgical implements are used when performing the surgical procedure is taught to the person.

A proficiency of the person is evaluated. A surgical implement selection system that includes a display portion and an input portion is provided. The first surgical implement tray is displayed on a first display region of the display portion. First images of the first surgical implements in the first display region are selected which causes the first images of the selected first surgical implements to appear in a second display region of the display portion. Each of the first images includes one of the first surgical implements.

The person organizes the first images in the second display region in a testing order based upon when the first surgical implements are used when performing the surgical procedure The testing order is compared to the actual order. The person is certified to have proficiency if the testing order matches the actual order.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 9 is a second portion of a product training test.

DETAILED DESCRIPTION OF THE PREFERRED EMBODIMENTS

Figure 1:
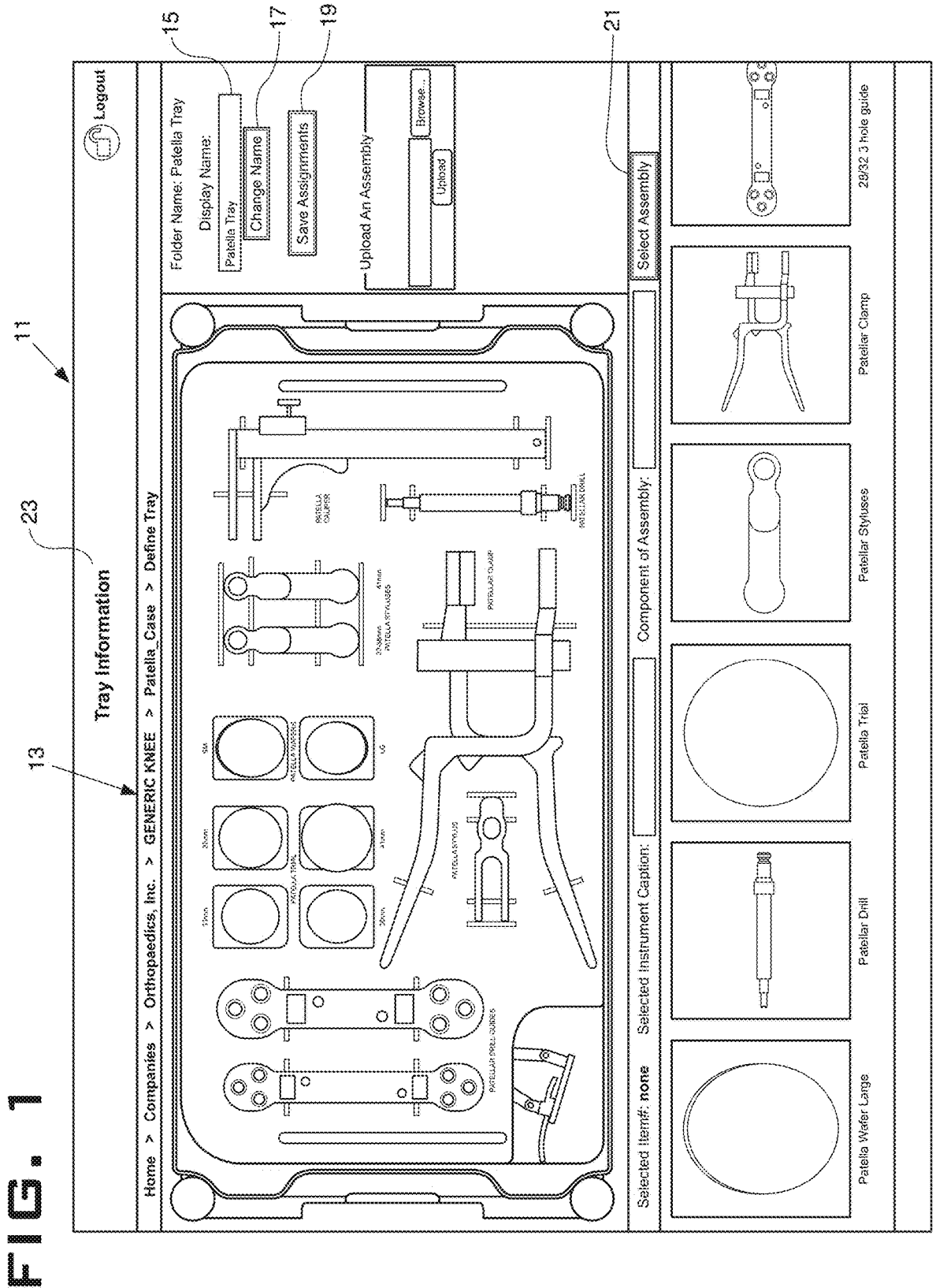
FIG. 1 is a screen view showing a layout of instruments in a define tray mode according to an embodiment of the surgical instrument selection system.

An embodiment of the invention is directed to a surgical implement training process, as described herein and illustrated in the associated figures. As used herein, the term surgical implement encompasses products that are used in conjunction with performing surgical procedures. Non-limiting examples of surgical implements include surgical instruments and surgical implants.

The surgical implement selection system may include a programming mode and an operating mode. The surgical implement selection system may also include a training mode and a tray assembly mode.

The surgical instrument selection system may broadly include at least two components—a display portion and an input portion. The surgical instrument selection system can be implemented in conjunction with a variety of different devices that include the display portion and the input portion. Examples of these devices include but are not limited to desktop computers, notebook computers, tablet computers and mobile phones.

The display portion may have different configurations based upon the device on that is used. For example, if the device is an iPad tablet computer, the information presented on the display portion may be optimized for a display width to height ratio may be about 4:3. On the other hand, if the device is a television or video monitor, the information presented on the display portion may be optimized for a display width to height ratio of about 16:9.

Depending on factors such as the type of device being used and the location of the device in the operating room, it may be preferable for the device to be powered using an on-board battery. Such a configuration eliminates the need for the device to be connected to an external power source while being used in the operating room. Such power cords could complicate the sterilization process. The power cords could also pose a hazard to persons present in the operating room during the surgical procedure.

As opposed to having the display portion directly associated with the system, it is possible for the display portion to be projected onto another surface. One such option for the projected display is for the image to be projected onto the back table where the surgical technologist or similar person could view image while looking at the instrument trays and associated instruments that are positioned on the back table.

This configuration would minimize the need for the surgical technologist to look up from the back table. This configuration would also minimize the potential of infection caused by the presence of a physical object within the sterile field as is discussed in other portions of the present application.

Yet another configuration for the display portion would be projected on a wall in the operating room or displayed on a monitor or other similar device that is mounted within the operating room. Examples of two such possible mounting locations are on a wall within the operating room or on a bracket that is attached to the ceiling in the operating room.

While such a configuration may require the surgical technologist to look up from the back table, this configuration would enable other persons in the operating room such as a surgeon to view the display.

The input portion may be integrated with the display portion such as in a touch screen that is typically found on tablet computers. The touch screen may provide an enhanced ability to use the system because the user only has to look at a single area to view the display portion and then input data on the touch screen.

The input portion may also assume a variety of configurations using the concepts of the invention. One such configuration of the input portion is a conventional mouse that is moved along a surface. Once the mouse is moved until the associated mouse pointer is positioned proximate to a desired location on the display portion, a button on the mouse may be pressed.

Still another possible configuration for the input portion is a keyboard. The keyboard may include actual keys. Alternatively, the keyboard may be virtual in that the keyboard is depicted on the display portion.

The device may be associated with a server from which the device obtains data. The server may be operated by and/or maintained by a variety of parties that are associated with the device. For example, the server can be maintained by the surgical device manufacturer, the surgical device distributor, the hospital, a governmental agency or combination thereof.

Depending on factors such as the type of device and the location of the device in the operating room, it may be necessary to sterilize the device before the device can be positioned within the sterile field in the operating room so that the device does not lead to an infection potentially being transmitted to the patient.

In certain situations, it may not be possible to subject the device to conditions needed to sterilize the device because the sterilization temperatures, pressures and/or chemicals may cause damage to the device. In such situations, portions of the device that are positioned in the sterile field during the surgical procedure may be placed within a sterile enclosure 40.

A challenge with using the device in conjunction with a sterile enclosure is the ability to accurately utilize the touchscreen or other input device associated with the device when controlling the operation of the device.

In one such configuration, the sterile enclosure 40 includes a front panel 42 and a side panel 44 that extends from at least one of the edges of the front panel 42. At least a portion of the front panel 42 may be fabricated from a transparent material. The transparent material may have sufficient clarity so that a user can readily see the information that is being displayed on the device.

The material used to fabricate the front panel 42 should be selected to prevent any organisms and chemicals that are present on the device from passing therethrough and, as such, presenting a contamination risk to the patient on which the surgical procedure is to be performed. An example of one such material that may be used to fabricate the front panel 42 is poly vinyl chloride.

The front panel 42 should also facilitate using the touchscreen input aspects of the device. The front panel 42 may exhibit an attraction to the display portion. The attraction may be provided through an electrostatic interaction between an inner surface of the front panel 42 and the display portion.

The attraction may also be provided by an adhesive 46 that is positioned on at least a portion of the inner surface of the front panel 42. In one such configuration, the adhesive 46 is provided over substantially all of the inner surface of the front panel 42. In another configuration, the adhesive 46 may be positioned along at least one of the edges of the front panel 42.

In configurations that utilize the adhesive 46, the adhesive should resist movement of the front panel 42 with respect to the device while not leaving any of the adhesive residue on the surface of the device when the sterile enclosure 40 is detached therefrom after the surgical procedure is completed because it will typically be desirable to discard the sterile enclosure 40 after each surgical procedure is completed as part of the process of preparing the operating room for the next surgical procedure.

The front panel 42 should also be fabricated from a material that is suitable for the sterilization technique that is used during the fabrication of the sterile enclosure. An example of one technique that may be used for sterilizing the front panel 42 is by exposure to ethyleneoxide gas.

Figure 7:
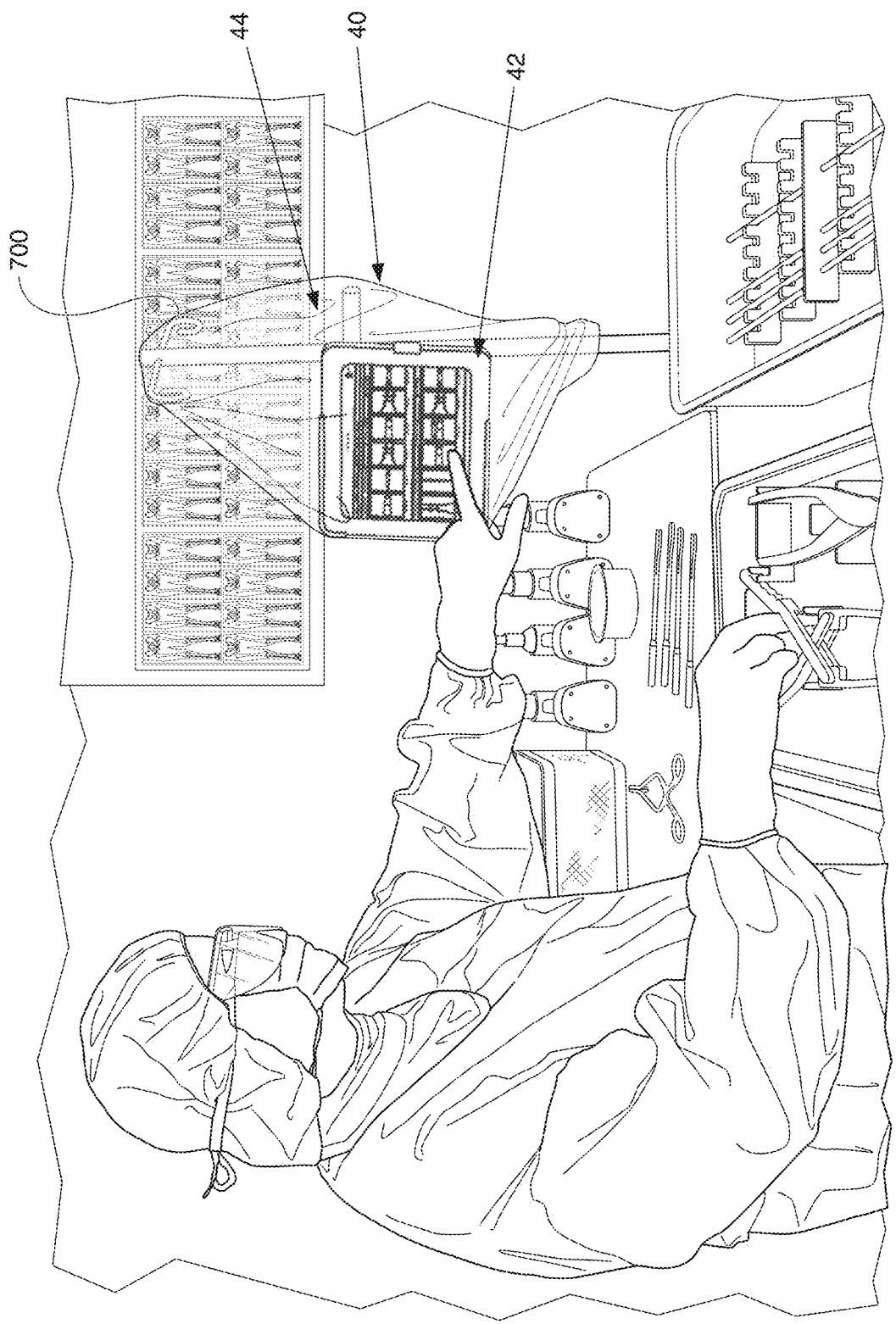
FIG. 7 is a front view of the surgical instrument selection system used in conjunction with a sterile enclosure.

As illustrated in FIG. 7, the side panel 44 may extend from each of the edges of the front panel 42. In one such configuration, the side panel 44 is formed with a length that is sufficiently long so that the end of the side panel 44 that are distal from the front panel 42 may be gathered or otherwise attached together behind the device.

One technique that may be used to hold the distal end of the side panel 44 is a clamp 700. Because the clamp is used on a back surface that is not intended to be contacted by a person in the sterile field within the operating room, the clamp may not need to be sterilized.

Alternatively or additionally, an adhesive may be provided on the distal end of the side panel 44. In one configuration, the adhesive may engage a back surface of the device to retain the sterile enclosure 40 in a stationary position with respect to the device.

The side panel 44 may be fabricated from a material that is readily sterilizable using techniques that are typically used for sterilizing equipment and supplies that are intended to be used in the operating room. An example of one suitable technique that may be used for sterilizing the side panel 44 is by exposure to ethyleneoxide gas.

The material used to fabricate the side panel 44 should be selected to prevent any organisms and chemicals that are present on the device from passing therethrough and, as such, presenting a contamination risk to the patient on which the surgical procedure is to be performed. An example of one such material that may be used to fabricate the side panel 44 is non-woven fabric that is manufactured from low density polyethylene.

A variety of techniques may be used to attached the side panel 44 to the front panel 42. Examples of such suitable techniques include an adhesive that is used alone or in conjunction with a mechanical fastener such as stitches.

While it is possible to fabricate the side panel 44 from the same material that is used to fabricate the front panel 42, fabricating the side panel 44 from a material that is more flexible than the front panel 42 may facilitate placing the sterile enclosure 40 over the surgical instrument selection system 10 and facilitate attaching the sterile enclosure 40 to the surgical instrument selection system 10.

The side panel 44 may be configured to extend substantially transverse to the front panel 42 such that the side panel 44 and the front panel 42 define a recess that is adapted to receive the surgical instrument selection system 10.

At least one of the front panel 42 and the side panel 44 may be fabricated from a material that is adapted for transmitting sound therethrough so that a speaker and/or a microphone on the device may be used while the device is in the enclosure.

As opposed to facilitating sound transfer through the entire front panel 42 or the side panel 44, a sound transmitting region may be provided on at least one of the front panel 42 and the side panel 44 proximate to where the speaker and microphone on the device.

Another example of a sterile enclosure is a bag in which X-ray cassettes are placed in prior to use in the operating room. The X-ray bag may enable the touch screen functionality to be utilized from outside of the X-ray bag.

The device may communicate with the server using a variety of communication techniques. One such communication technique is via at least one wire that extends between the device and the server.

Another suitable communication technique involves a wireless communication protocol that links the device and the server. Non-limiting examples of the wireless communication protocols include Wi-Fi, Bluetooth and 3G.

The system may operate in a variety of modes using the concepts of the invention. One such suitable mode is for the data to be transmitted to the device upon request. For example, the data could be presented in a web-based format and when selections are made, different images or web pages may be retrieved by the system. Such a system would provide a real-time transfer of data between the device and the associated server.

One potential drawback of such a configuration is that if the communications link between the system and the data provider is broken or if the quality or speed is degraded, it would not be possible for additional images to be displayed on the system or the images may be displayed slower than is needed during the surgical procedure. If this happened during a surgical procedure, the surgical technologist would not receive information on which surgical instruments were to be selected in a timely manner, which could impact the flow of the surgical procedure and result in the patient experiencing complications.

Another mode for operating the system is to store the data on the device. Factors such as the number of surgical instruments and surgical instrument trays and the resolution of the associated images would determine the amount of storage space that the device would be required to have.

While this configuration would avoid the requirement for a communication link to be continuously provided, the device should at least periodically attached to a communication link so that the data stored therein could be updated such as in response to a change in the instructions for use that have been approved by the Food and Drug Administration.

One possible configuration would be to have the device check for updates during hours in which the device is not typically used. For example, the device could check for updates between about 1:00 am and 4:00 am. Such a configuration would balance the desire to have up-to-date data on the device with the desire not to have the data downloading as needed during a surgical procedure.

Because of the importance of periodically updating the device to ensure that the device includes the most up to date configuration, the operation of the device may be at least partially disabled if the device has not been able to check for updates within a specified period of time. In certain embodiments, it may be necessary for the device to check for updates at least every month.

When the device is used in conjunction with surgical techniques that are more likely to change such as when the surgical technique is one that is undergoing regulatory approval, it may be necessary for the device to check for updates every 7 days to about every 14 days.

If the device is not able to successfully check for updates within the specified period of time, the ability to use the device in conjunction with performing a surgical procedure may be restricted.

Alternatively or additionally, the aspects of the surgical procedure may be configured to automatically delete after a selected period of time. In such a configuration, when it is attempted to use the device after the selected period of time has passed, the screens where the images of the surgical instruments and/or surgical instrument trays are typically displayed may be blank because the stored data has been deleted.

The date by which the update is required may be displayed on the device so that a person using the device would be able to confirm that the device has been appropriately updated. In one such configuration, the update check deadline may be displayed on an initial screen when the user turns on or begins running the surgical instrument selection system.

The update check deadline may be prominently displayed on this initial screen so that a person who will be using the surgical instrument selection system would readily see this information and be able to confirm whether the surgical instrument selection system needs to check for an update.

Alternatively or additionally, the update check deadline may be displayed on at least one of the screens while the surgical instrument selection system is being used. For example, the update check deadline may be displayed proximate to one of the corners of the display.

This update check deadline may be presented in a relatively small size compared to the overall size of the display such that the update check deadline may be readily viewed but so that this information does not impact the ability to use the surgical instrument selection system.

To minimize the potential of the user not being aware of the need to update the device as a requirement of being able to continue using the device, the device may display at least one notification prior to the device becoming unusable. In one such configuration, at least one notification is displayed about 1 week before the device becomes unusable. A notification may also be displayed about 1 day before the device becomes unusable.

The device may also include a notification system that periodically checks for updates of the data stored on the device. If it is determined that an update of the stored data is available, a message may be displayed on device.

Depending on the importance of the update, it may be possible for the update to be postponed until a later date. When the update is of particular importance, it may not be possible for the update to be delayed such that it is not possible to continue using the device until the update is installed.

In addition to or as an alternative to displayed the stored update notification on the device, a notification of the availability of the update may be provided to another person who is associated with the maintenance of the device.

To prevent unauthorized use of the device, it may be necessary for the device to connect to a database before each time that it is desired to use the device. Such a system could prevent use of a stolen device. Such a process could also be used to prevent use of the device when the license fee has not been paid.

In still another configuration, the device may include functionality to erase the memory of the device by transmitting a command to the device. In addition to or as an alternative to erasing the memory of the device, the command may disable the device to prevent such unauthorized use.

The device may display a variety of information that may be used to identify the surgical instruments. One such way to identify the surgical instruments is by providing images of each of the surgical instruments.

In certain embodiments, the image may be taken from a single perspective in which surgical instrument is oriented so as to best view the structural features of the surgical instruments. To maximize the size of the surgical instrument in the image, the surgical instrument may be oriented at an angle in the image. In one such configuration where the surgical instrument has an elongated configuration, the surgical instrument may be oriented at an angle of about 45°.

It is also possible for multiple images to be provided for each surgical instrument in which the various images show different orientations of the surgical instrument. The user could switch between the available images such as by tapping on the image.

In still other embodiments, a three-dimensional illustration of the surgical instrument may be provided. The input device may include the ability to manipulate the surgical instrument to different orientations. For example, when the user slides his/her finger over the image in a first direction, the image may rotate in the first direction.

It is also possible to display additional information that may be used to identify the surgical instrument. Examples of such additional identifying information include the name of the surgical instrument, the part number of the surgical instrument, the manufacturer of the surgical instrument and the type(s) of surgical procedures on which the surgical instrument may be used.

In certain embodiments, it may be desirable to minimize the presence of additional information on the display so as to enhance the ability of the person using the device to clearly see the features of the surgical instrument illustrated in the image. When such a configuration is used, it may be possible for at least some of the additional details referenced above to be viewed such as be tapping or otherwise selecting the image.

The display may also include images of the surgical instrument trays. Similar to the surgical instrument images, the tray images may be taken from a single perspective in which surgical instrument tray is oriented so as to best view the contents of the surgical instrument trays. It is also possible for multiple images to be provided for each surgical instrument tray in which the various images show different orientations of the surgical instrument tray.

In still other embodiments, a three-dimensional illustration of the surgical instrument tray may be provided. The input device may include the ability to manipulate the surgical instrument tray to different orientations.

It is also possible to display additional information that may be used to identify the surgical instrument tray. Examples of such additional identifying information include the name of the surgical instrument tray, the part number of the surgical instrument tray, the manufacturer of the surgical instrument tray and the type(s) of surgical procedures on which the surgical instruments in the surgical instrument tray may be used.

In certain embodiments, it may be desirable to minimize the presence of additional information on the display so as to enhance the ability of the person using the device to clearly see the features of the surgical instrument tray illustrated in the image. When such a configuration is used, it may be possible for at least some of the additional details referenced above to be viewed such as be tapping or otherwise selecting the image. The availability of the additional information may be indicated by a variety of techniques such as by providing the image with a different background color or by including an icon on the image display.

The template may be viewed in a variety of different manners. One suitable manner for viewing and editing the template is using a browser such as is used for conducting internet searches. An advantage of using a browser is that the template may be viewed and/or edited using a variety of different types of computers and/or operating systems.

Alternatively, the surgical instrument selection system may be provided in the form of an application that is installed on the device on which the surgical instrument selection system is intended to be used.

A potential advantage of using an application that is installed directly on the device on which the surgical instrument selection system is used is that such a process may allow for additional functionality such as connection to peripherals and/or operation of such peripherals that is not available when the surgical instrument selection system is utilized on conjunction with a browser.

Another potential advantage of using an application that is installed directly on the device on which the surgical instrument selection system is used is that such an implementation may provide an enhanced level of security compared to using the surgical instrument selection system in conjunction with a browser.

The images of the various surgical instruments used during a particular surgical procedure may be placed into order based upon when the surgical instruments will be used. In certain embodiments, a template 100 may be created that includes the surgical instruments and/or implants oriented according to instructions for use that have been approved by a governmental entity such as the US Food and Drug Administration. An example of one such template is illustrated in FIG. 1.

This template 100 may be created by a variety of different parties. For example, the template may be created by the entity that manufactures and/or programs the device. The template may also be created by the entity that manufactures and/or distributes the surgical instruments. In still other situations, the template may be created by someone affiliated with the hospital where the device is to be used. An example of one such person affiliated with the hospital is the surgeon who will be using the surgical instruments.

If the template 100 is modified from the approved instructions for use and such modifications result in injury or death to a patient, there is the potential of significant liability to the person who made such modifications as well as the organization that the person is affiliated with. In view of the preceding risks, the ability to modify the template may be limited.

Furthermore, there is potential liability to the organization that obtained the regulatory approval for promoting the use of the surgical instruments and/or implants in a manner that is not in conformance with instructions for use that were approved by the governmental entity even if no one was harmed by such modifications.

Even though the regulatory approval process may restrict the ability of entities such as the manufacturer or distributor from recommending or suggesting that the surgical instruments or implants be used in a manner other than the process that has been approved by the applicable regulatory organization, the surgeon who will be using the surgical instrument or implant may desire to use a procedure that is different from the procedure that has received regulatory approval.

As such, in situations where the template is prepared by someone other than the surgeon who will be using the device, the surgeon who will be using the device may be given the opportunity to customize the template.

Figure 2:
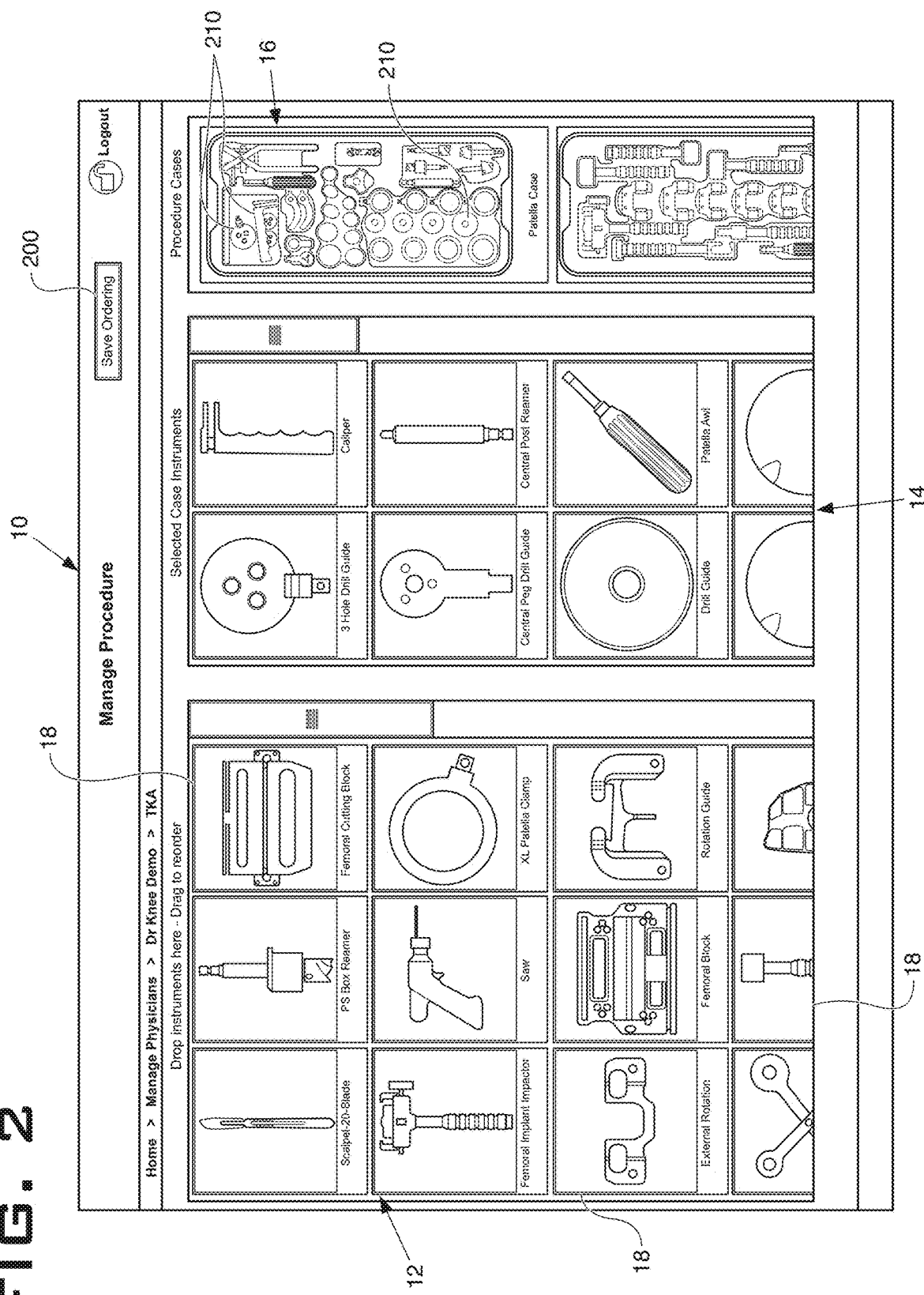
FIG. 2 is a screen view that includes a tray view window, a selected tray instruments window and an ordered instrument window.

To assist in customizing the template, a customization mode may be provided. A display associated with the customization mode is illustrated in FIG. 2. The customization mode display 10 includes an available instrument window 12 and a selected instrument window 14. The customization mode display 10 may also include a tray view window 16.

Images 18 may be selected in the available instrument window 12 and then dragged to the selected instrument window 14. Once the images 18 are in the selected instrument window 14, the images 18 may be selected and then moved to a different location within the array of images 18 in the selected instrument window 14.

When one of the images 18 in the available instrument window 12 or the selected instrument window 14 is selected, the location of the surgical instrument or implant depicted in such image may be identified in the tray view window 16.

The tray view window 16 may also identify each of the surgical instruments or implants that has been moved to the selected instrument window 14. In one such configuration, a mark 210 may be placed adjacent to or at least partially over each of the surgical instruments or implants that has been moved to the selected instrument window 14.

While such a mark should be sufficiently large so that the mark is readily seen by a person using the surgical instrument selection system, the mark should not be sufficiently large to impede viewing of the surgical instrument or implant.

Using such a process, the person creating or modifying the template can be provided with feedback on which of the surgical instruments or implants has or has not been used as part of a confirmation that the surgical instrument selection system has been correctly configured.

The customization may include adding images, deleting images, moving images or combination thereof. The customization may also include adding materials other than images. Examples of such customizations include textual notes, audio files, video files or combinations thereof.

In one configuration, the customization may have at least two levels. A first customization level may be limited to adding textual comments or annotations that are viewed by the person who is using the surgical instrument selection system.

A second customization level may provide the user with the ability to customize the template further such as by adding images, deleting images and moving images. The second customization level may limit the user to selecting surgical instruments and/or implants that are included in the instrument and/or implant trays that were previously associated with the template.

A third customization level may provide the user with the ability to customize the template in any manner in which the user desires. Such customization could include adding or deleting instrument and/or implant trays that are associated with the template as well as adding, deleting or modifying textual notes, audio files and video files. Depending on the extent of the customization, additional templates may be defined.

The customizations may be intended to assist the person using the device such as the surgical technologist. The customizations may also be used by other persons that are present in the operating room where the device is being used. For example, the customization may advise the surgeon about potentially complicating factors associated with the surgical procedure.

In one configuration, the customization is done directly on the device on which the surgical instrument selection system is being used. In this situation, the customized template may be stored on the device.

To minimize the potential of the customizations being lost such as if the device is stolen, broken or otherwise becomes unusable, the customized template may be copied to a local storage device that is directly connected to the device. In another configuration, the customized template may be backed up such as onto a server that is used by the entity that distributes the surgical instrument selection system.

In another configuration, the template is customized using a device other than the device on which the surgical instrument selection system is used. An example of one such system for customizing the template is through a secure website that is accessed by entering a login name and password. This website may be associated with the entity that distributes the surgical instrument selection system. The communication between the user and the server may be encrypted to minimize the potential that there is unauthorized access to the surgical instrument selection system.

The customization process may be similar to the customization process that is used directly on the device. Once the customization process is completed, the user may request that the customized template be downloaded to the device. Similar to the update process that is described in more detail herein, once the device is alerted of the availability of the update, the device may display a notification such as the next time the device is turned one. Thereafter, the customized template is downloaded and installed onto the device.

Once the customized template is installed on the device, the surgical instrument selection system may display a notice to users that the template being used has been customized. This notice may be displayed on the initial screen when the surgical instrument selection system begin running as well as on the display while the surgical instrument selection system is running.

Once the template has been customized, the template may be converted to a read-only or intra-operative mode, which prevents any further modifications to the template. It may be desirable for the template to be in a read-only mode when used in conjunction with a surgical procedure to prevent the template from being intentionally or inadvertently modified by someone who is not authorized to make such changes.

This read-only mode may be referred to as the intra-operative mode. In certain situations, the device may display a textual and/or graphical designation that indicates that the surgical instrument selection system is in the intra-operative mode in which revisions are prohibited.

The template may be converted to read-only mode by a limited group of persons to ensure that the integrity of the modified template is retained. Examples of persons who may be able to convert the template to read-only include the surgeon who will be using the device, someone affiliated with the hospital administration where the device will be used, the surgical instrument manufacturer and the entity that distributes the device.

To ensure that the final template is accurate and complete, the person converting the template to read-only may have to review the modified template to ensure that there are no errors in the template. Depending on factors such as the complexity of the surgical procedure, the hospital may include a template approval protocol that sets forth the conditions under which a revised protocol must be reviewed before the protocol is approved for use in conjunction with a surgical procedure.

The template approval protocol may track each of the revisions that have been made to the protocol. This tracking protocol may include the identity of the person making the changes along with the day and/or time when each of the revisions was made to the protocol. The tracking protocol may also track the identity of the person(s) who reviewed and/or approved the revisions along with the day and/or time when each of the reviews and/or approvals were made to the protocol.

The revision date and/or revision number may be displayed on the device so that a person using the device would be able to confirm that the device has been appropriately updated. In one such configuration, the revision date and/or revision number may be displayed on an initial screen when the user turns on or begins running the surgical instrument selection system.

The revision date and/or revision number may be prominently displayed on this initial screen so that a person who will be using the surgical instrument selection system would readily see this information and be able to confirm that the surgical instrument selection system is up to date.

Alternatively or additionally, the revision date and/or revision number may be displayed on at least one of the screens while the surgical instrument selection system is being used. For example, the revision date and/or revision number may be displayed proximate to one of the corners of the display.

This information may have a relatively small size compared to the overall size of the display such that this information may be readily viewed but so that this information does not impact the ability to use the surgical instrument selection system.

Figure 3:
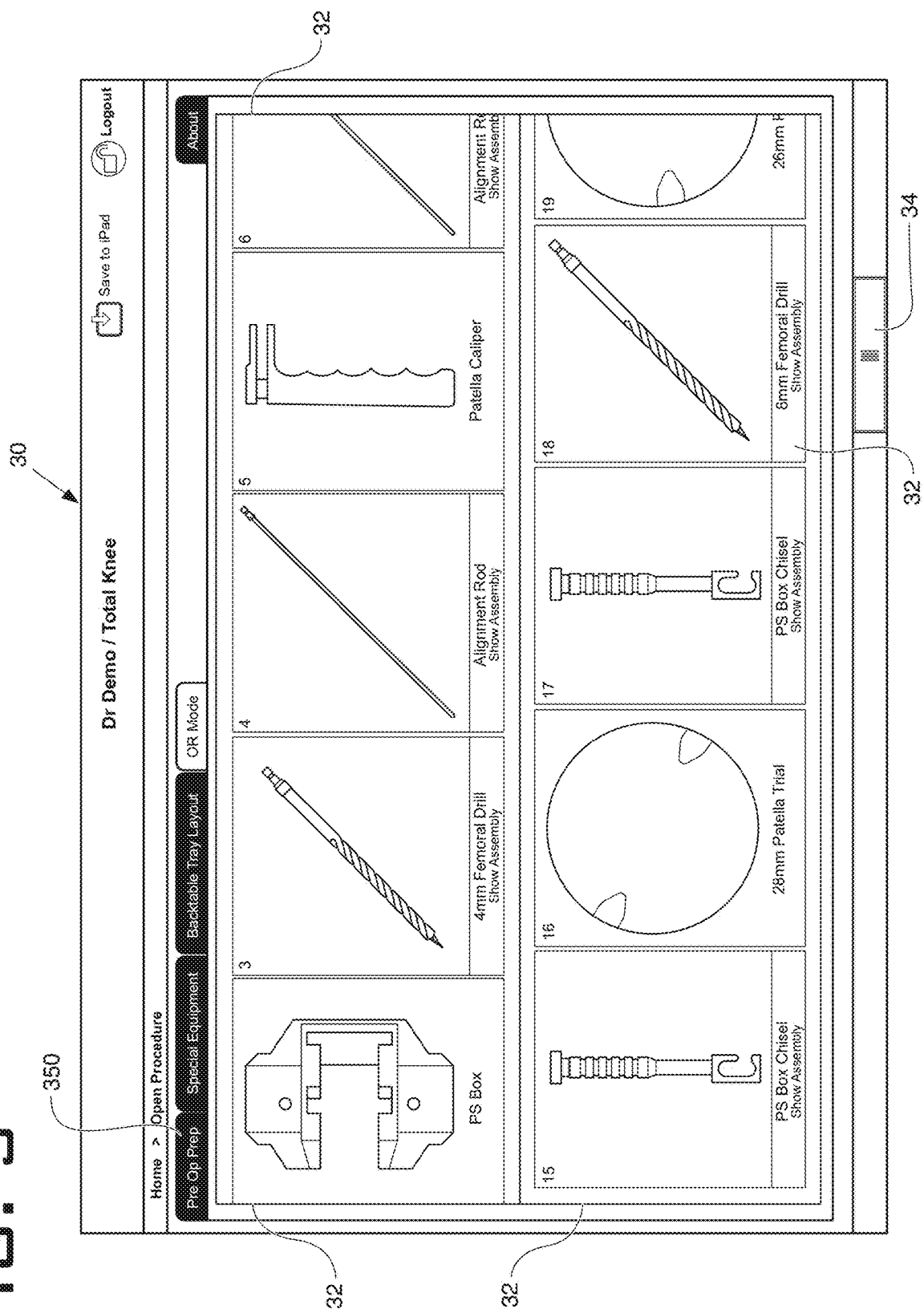
FIG. 3 is a screen view in an intra-operative mode according to an embodiment of the surgical instrument selection system.

Thereafter, the device may be used in conjunction with a surgical procedure. An example of a display 30 on the device is illustrated in FIG. 3. The display 30 includes a plurality of images 32 that are arranged in the order in which the particular surgical instruments are to be used. Depending on the size of the images 32 and the direction in which the images 32 will be viewed during the surgical procedure, the images 32 may be arranged in at least one row or at least one column.

To assist a user in determining the order in which the surgical instruments are to be used, a number and/or letter may be associated with each of the images 32. For example, the number may be provided proximate a lower corner of each of the images 32.

In certain embodiments where it is not possible for all of the images 32 to be displayed on the display 30 at one time, a slider 34 such as illustrated proximate the bottom of FIG. 3 may be provided on the display 30 to facilitate manipulating the display 30 for viewing the images 32.

Alternatively or additionally, the images 32 may be configured in a plurality of pages that may be viewed in sequence. The device may include either a physical button or a virtual button that may be used to cause different pages of images 32 to be displayed.

To assist the surgical technologist in quickly locating the correct surgical instrument, an image of the surgical instrument tray in which the surgical instrument is located may be displayed when the image is pressed. In addition to displaying the surgical instrument tray, the location of the surgical instrument in the surgical instrument tray may be identified.

Once such technique for identifying the surgical instrument in the surgical instrument tray is with an arrow that is pointing at the surgical instrument. Another such technique for identifying the surgical instrument in the surgical instrument tray is outlining the surgical instrument in a color that contrasts from the other colors used in the surgical instrument tray.

Figure 4:
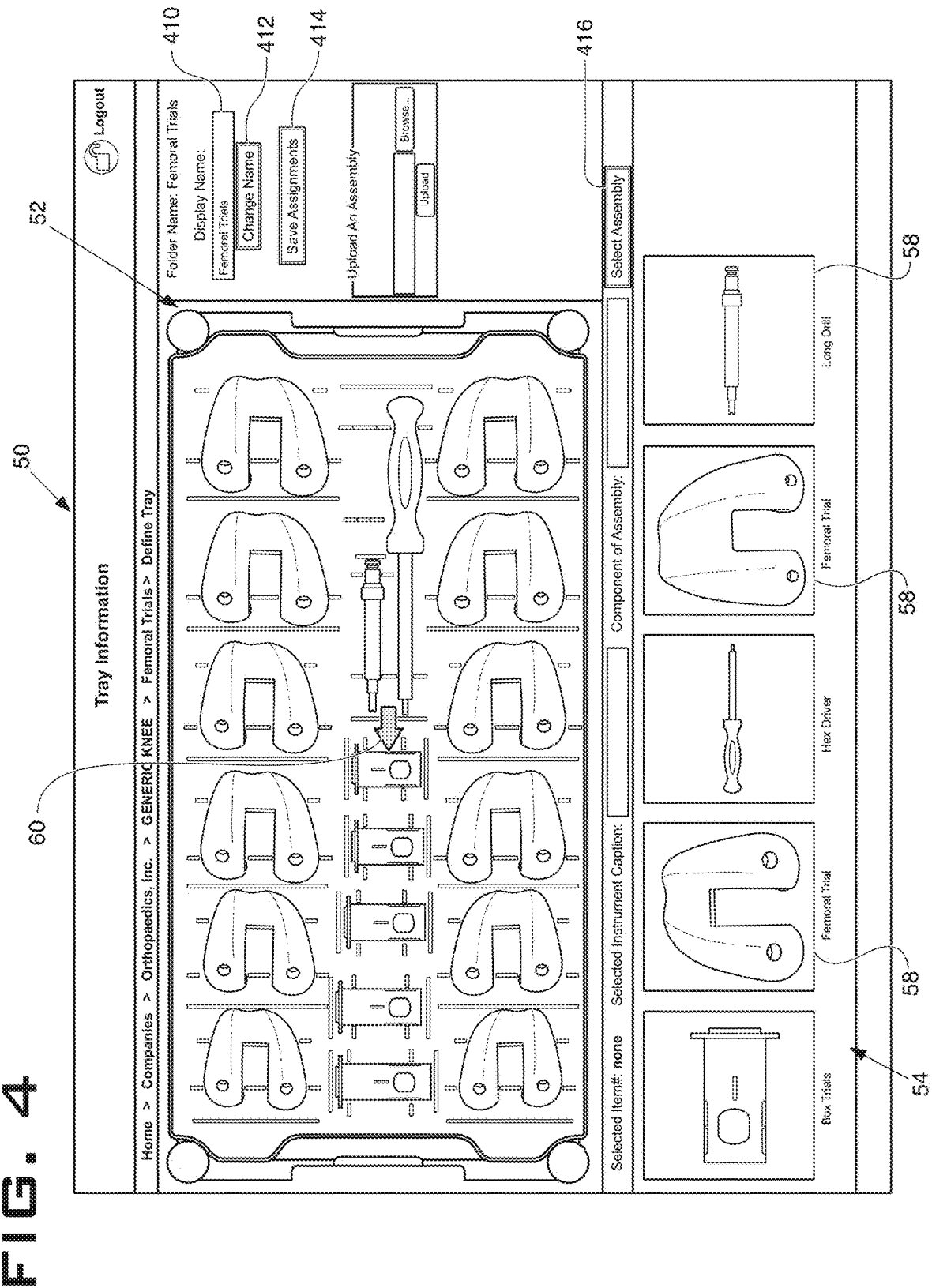
FIG. 4 is a screen view with a tray view window and a selected instrument window that is adapted for use in conjunction with femoral surgery.

Another configuration of the procedure mode that is directed to femoral implant tools is illustrated in FIG. 4. The display 50 includes a surgical instrument tray window 52 and a surgical instrument window 54. The surgical instrument tray window 52 contains an image 56 of the femoral implant tray that includes a plurality of surgical instruments. The surgical instrument window 54 includes images 58 of individual surgical instruments along with identifying text.

When one of the surgical instruments is selected from the surgical instrument window 54, identifying information may be provided for the selected surgical instrument. Examples of the identifying information include the name of the selected surgical instrument and/or the reference number associated with the selected surgical instrument.

Additionally, selection of one of the surgical instruments in the surgical instrument window 54 may cause the location of the selected surgical instrument in the surgical instrument tray to be identified such as be using arrow 60.

Figure 5:
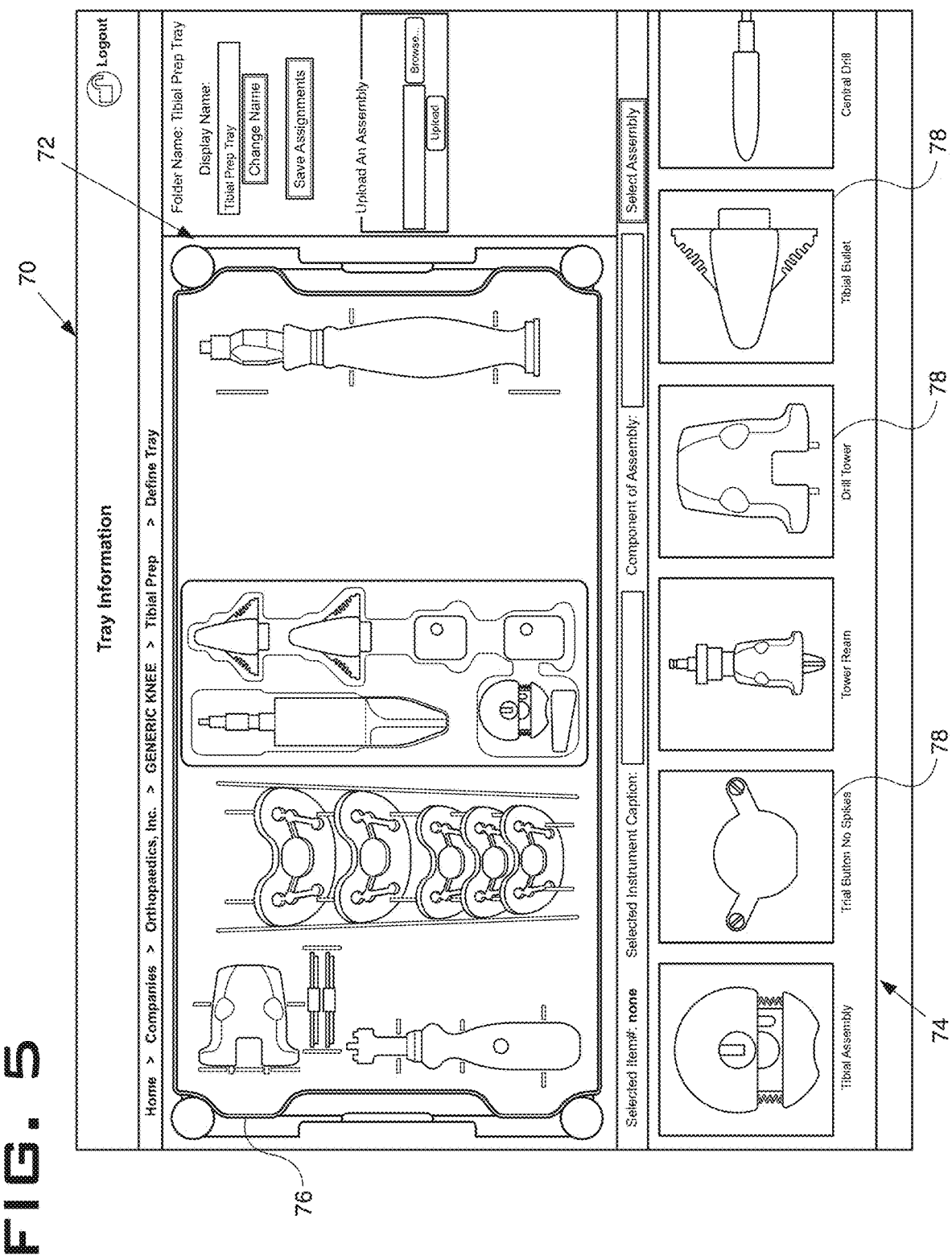
FIG. 5 is a screen view with a tray view window and a selected instrument window that is adapted for use in conjunction with tibial surgery.

Another configuration of the procedure mode that is directed to tibial implants is illustrated in FIG. 5. The display 70 includes a tibial implant tray window 72 and a tibial implant window 74. The tibial implant tray window 72 contains an image 76 of the tibial implant tray that includes a plurality of tibial implants. The tibial implant window 74 includes images 78 of individual tibial implants along with identifying text. While the instrument trays are suited for a variety of implants, the illustrated tray is used for tibial implants.

When a particular tibial implant is selected in the tibial implant window 74, the location of the particular tibial implant is identified in the tibial implant tray window such as with an arrow 78. Using this procedure, the surgeon may take measurements of the tibia where the implant is to be inserted. Thereafter, the measurements are used to select the appropriate tibial implant so as to ensure the correct fit.

As an initial step in using the intra-operative mode, it may be required for the surgeon who will be performing the surgical procedure to enter a user name and/or password to gain access to the surgical instrument selection system.

Alternatively or additionally, it may be required that the surgical technologist who will be assisting with the surgical procedure to enter a user name and/or password to gain access to the surgical instrument selection system.

Such a process may be used to ensure that the surgeon selects the correct surgical procedure to be displayed on the surgical instrument selection system. This process also enables the surgeon to ensure that the device on which the surgical instrument selection system is being used has the correct version.

The process could also be used as part of a logging procedure that tracks the number of times the surgical instrument selection system has been used for performing each procedure as well as the surgeon and surgical technologist who used the surgical instrument selection system.

This log in process could also be used to restrict the use of the surgical instrument selection system to only surgeons and/or surgical technologists who have been approved by the medical facility to perform the particular surgical procedure.

In addition to or alternatively to the uses that are set forth above, the system may be used to track which surgical instruments are actually used during a surgical procedure. Tracking what surgical instruments are used during a particular type of surgical procedure may be beneficial in a variety of situations.

One such potential benefit of tracking what surgical instruments are used during a procedure is to determine if one or more of the surgical instruments are consistently not used during a particular type of surgical procedure. In such situations, the instrument manufacturer and/or the hospital may review whether it is desirable to continue including the unused surgical instruments in the surgical instrument trays.

Removing certain unused surgical instruments from the surgical instrument trays would not only reduce the cost associated with the surgical instrument trays. Furthermore, reducing the number of surgical instruments in the surgical instrument trays could also potentially lead to a reduction in the number of surgical trays and/or a reduction in the number of instruments in the surgical instrument trays. Both of these factors could enhance the ability of the surgical technologist to provide the surgical instruments to the surgeon accurately and in a timely manner.

Tracking what surgical instruments are used during a surgical procedure could also enable an alert to be issued if such non-use of the surgical instrument is believed to be indicative that an aspect of the surgical procedure has been omitted.

Depending on the perceived significance of the non-use of the surgical instrument, the alert could be issued during the surgical procedure proximate to when the surgical instrument was to be used. Alternatively or additionally, the alert could be issued after the completion of the surgical procedure. Sending the alert after the completion of the surgical procedure may be preferable when it is unlikely that the non-use of the surgical instrument would significantly decrease the likelihood of the surgical procedure being successful.

Tracking of what surgical instruments that have been used can be done using a variety of mechanisms. One such mechanism of indicating that the surgical instrument has been used is for the person using the system of the invention is to click on or otherwise select the image.

Another way of tracking what surgical instruments have been used is to associate a scanning device with the system. The scanning device may assume a variety of forms. One such form for the scanning device is to read a bar code or other type of identifying indicia that is provided on a surface of the surgical instrument.

The scanning device could utilize alternative technologies such as RFID. In such situations, an RFID tag may be provided on a surface of or within the surgical instrument. Examples of the identifying indicia include but are not limited to product manufacturer, product name, product number, product lot number, and product serial number.

The system of the invention may also be used to track the timing of various aspects of a surgical procedure. In one configuration, the system may track the overall time of the surgical procedure. The system may also be used to track the amount of time that lapses between different surgical instruments being used.

Tracking of the length of time may be done using a variety of mechanisms. One such suitable mechanism is providing a separate timer function that may be engaged such as by pressing a button on a surface of the display.

While it is possible for the individual aspects or overall lengths of time to be displayed on the system, it is also possible to track the time periods without displaying them on the system. Not displaying the individual or overall time periods may eliminate the desire for persons present in the operating room during the surgical procedure to monitor the time while the surgical procedure is being performed.

Monitoring the duration of aspects of the surgical procedure by persons present in the operating room could be perceived as causing the surgeon or others in the operating room to compete to complete a surgical procedure more quickly possibly affecting the patient care and/or safety.

The length of time associated with individual aspects or overall lengths of time may be recorded in a patient's chart. Alternatively or additionally, the lengths of time may be monitored by another entity such as the surgical instrument manufacturer. In such situations, information that could identify a particular patient or otherwise potentially lead to a release of confidential medical information may not be included with the timing information without receiving the patient's approval.

Recording the time periods associated with the surgical procedure may be used by the hospital to track aspects relating the utilization of the operating room. For example, the hospital may be able to better estimate the time associated with aspects of a particular surgery such as prepping the patient, conducting the surgical procedure and/or cleaning of the operating room after the surgical procedure is completed such that the operating room would be ready for the next surgical procedure.

The system may also be used to track information for billing patients for charges associated with the surgical procedure. For example, the system can be used to track when particular surgical instruments and/or surgical supplies are used during the surgical procedure.

Tracking of the surgical instruments and/or surgical supplies may be done using a variety of techniques using the concepts of the invention. One potential way of tracking the surgical instruments and/or surgical supplies may be by using a menu system that includes images, descriptions and/or codes for the various surgical instruments and/or surgical supplies that are used at the hospital. When an item is used, the image, description and/or code associated with the item are selected.

Alternatively or additionally, a scanning device may be associated with the system. When the item is used, the scanning device may be used to enter the product information into the hospital's billing system. The scanning device may take a variety of forms. Examples of the suitable forms of the scanning device include bar codes, RFID tags and combinations thereof.

The system may also be used to track the persons who are present in the operating room during the surgical procedure. One such suitable way to track the persons who are present in the operating room is to provide a module that includes information on the various hospital employees.

At some point before, during or after the surgical procedure the identification of the various persons present in the operating room during the surgical procedure may be recorded. The system may also be used to track the length of time that each of the persons was present in the operating room.

Depending on the manner in which the patient is billed for the surgical procedure, the length of time that particular persons are present in the operating room may be directly billed. In situations where the patient is not billed for the time individual persons were present in the operating room, the information about persons being present in the operating room may be used by an entity such as the hospital for other purposes. One such other purpose is tracking staffing levels in the hospital.

The system may include a notification module that periodically receives information from other sources relating to aspects of the surgical procedure. For example, the notification module may receive recall notices/warnings relating to the surgical procedures, surgical implants, surgical instruments and/or surgical supplies.

The notices may be provided by or obtained from a variety of sources. Examples of the sources of the notices include but are not limited to governmental regulatory organizations, surgical device manufacturers, surgical instrument manufacturers, hospitals and combinations thereof.

Depending on the manner in which the system is configured as is discussed in more detail above, the notices may be provided in a real-time basis during the surgical procedure. In such situations, the system may be configured to provide the notice to the persons while enabling the persons in the operating room to complete the surgical procedure.

The notices may also be transmitted to the system during periods of time in which the system is not being used such as between surgical procedures. The system may be programmed to automatically obtain the notices in evening hours after the system has not been used for a specified period of time.

The system may also be configured to issue a notice if the system has not been able to obtain updated notices for greater than a specified period of time. For example, if the system is not able to obtain notice updates for more than a 24 hour period, a message may be displayed on the system. Additionally or alternatively, the notice may be provided to other parties associated with the system. Examples of such other parties include the manufacturer of the system and the hospital where the system is used.

The notices can also be used to convey to the person operating the system such as the surgical technologist or the surgeon that educational materials and/or sessions are available relating to the system. The notices may also indicate when features of the system have been modified, added or deleted.

The system may also be used to record aspects of the surgical procedure. In certain embodiments, the recording may be limited to audio. However, in other embodiments, the recording may also include video. It may be desirable and/or necessary for the audio and/or video to be encrypted to reduce the potential of unauthorized access to the audio and/or video such as may be mandated by applicable health record or privacy laws.

In one such configuration, the system may record all of the audio in an operating room during a surgical procedure. The system may start recording such as when a patient is brought into the operating room and then stop recording when the patient is taken out of the operating room after the completion of the surgery. Such a configuration would provide a real-time record of what transpired in the operating room while the patient was undergoing the surgical procedure.

In another configuration, the audio recording may be limited to one or more of the persons in the operating room. For example, the audio recording may be done by the surgeon. Such an audio recording may be transcribed by a human, an electronic device or combination thereof. Since the audio recording is done during the surgical procedure, it may be more accurate than if the surgeon dictates a summary of the surgical procedure after the completion of the surgical procedure.

When the device includes a video display, a video camera and a speaker, the device can be used to conduct an interactive video dialog between a person who is located at a medical facility where the surgical instrument selection is being used and another person who is located at a different location. Examples of two such video communications systems that may be used are Skype and Facetime.

The invention thereby enables the expertise of a person who is not at the medical facility to be utilized by discussing aspects of a particular medical procedure either prior to performing the medical procedure, while performing the medical procedure or after performing the medical procedure.

Such a configuration enables a person with significant expertise to be utilized to a greater extent than if the person was physically present at the medical facility. This process thereby alleviates the need for the manufacturer or distributor of the surgical instrument or implant to avoid placing a representative at the medical facility while ensuring that any potential questions relating to the selection and use of the surgical instrument or implant can be answered in a timely manner.

Because there is a more efficient use of the remote person when compared to physically placing the representative at the medical facility, the manufacturer or distributor of the surgical instrument or implant can provide more knowledgeable person to answer questions while also reducing costs compared to having a representative present each time the surgical instrument or implant is used.

Figure 6:
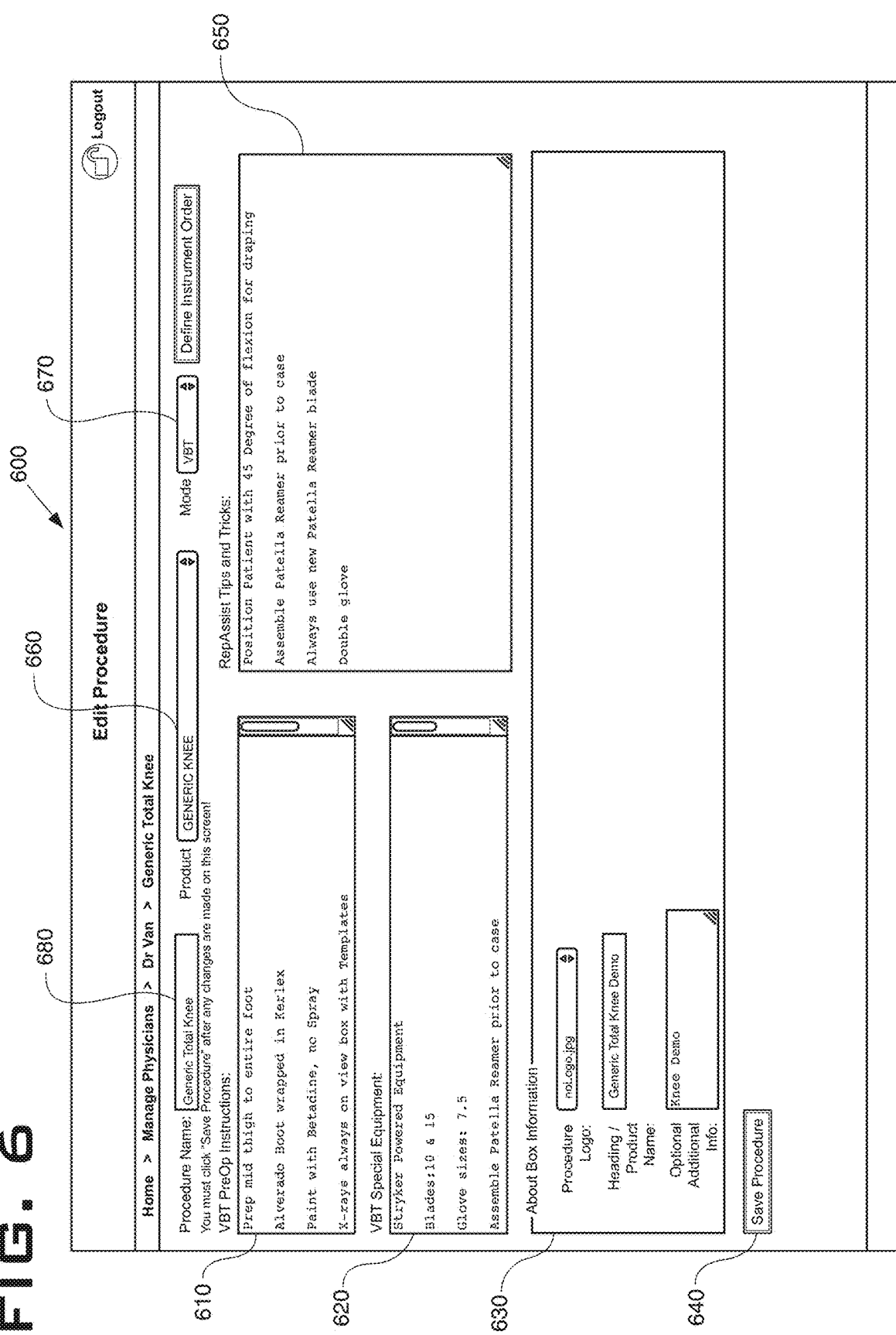
FIG. 6 is a screen view for defining preoperative instructions, operating room preparation and post-operative instructions as determined by the surgeon.

To ensure that no confidential aspects of the patient or the medical procedure being performed on the patient, the communication link between the device and the remote person may be encrypted in a manner that complies with the applicable governmental requirements such as Health Insurance Portability and Accountability Act of 1996, which may apply to medical facilities that are located in the United States The system may also be used to prepare post-operative orders for the patient. These orders may be prepared utilizing a variety of different factors. Examples of the factors include the surgical procedure, complicating factors that were identified during the surgical procedure and input from the surgeon(s) that performed the surgical procedure. FIG. 6 illustrates text for patient pre-operative instructions and post-operative instructions as well as instructions for preparing the operating room for the particular surgical procedure.

The post-operative instructions can include a variety of aspects such as restrictions on physical activity, medications and time periods within which the patient is required to follow up with the physician. The system can also be used to generate educational materials that may be distributed to the patient before or after the surgical procedure.

The system may also be used in conjunction with educational activities. Such educational activities may be conducted at a time period that is different than when the surgical procedure is performed.

In one such configuration of the educational activities, instructions are provided on the use of the system. For example, details may be provided on the process for operating the input device and how to move between different modes of the system.

The educational materials may be directed to a variety of different audiences. For example, the educational materials may be directed to person who would be providing support to a surgeon while the surgeon is performing a particular surgical technique such as a nurse or a surgical technician.

The educational materials may also be directed to persons that market surgical instruments and/or implants such as representatives that work for a surgical instrument manufacturer.

A benefit of using the surgical instrument selection system in conjunction with education is that the surgical instrument selection system may be used to teach the proper order in which the surgical instruments and implants are used by the surgeon. Because the surgical instrument selection system is configured based upon the instructions for use for a particular surgical instrument or implant that have been approved by a regulatory organization, there is no question that the person undergoing such training has been taught a procedure that is in conformance with the approved instructions for use. The invention thereby removes potential training differences resulting from different instructors teaching the procedures.

The hands-on nature of training conducted using the surgical instrument selection system also has the potential of reducing the training when compared to traditional training techniques where the person undergoing the training merely listens to the instructor or watches the instructor perform demonstrations with the surgical instruments or implants.

The surgical instrument selection system also provides an objective criterion to evaluate the proficiency of the person who has undergone the training. This objective training criteria enables the manufacturer or distributor of the surgical instrument or implant to certify that the person who underwent the training to have obtained a certain proficiency with respect to aspects such as the identification of the individual components of the surgical instrument or implant as well as the order in which the surgical instruments or implants are used when performing a particular surgical technique in a manner that has been approved by the applicable regulatory organization.

The educational materials may also be used to educate a person on aspects of the surgical instruments that are displayed on the surgical instrument selection system. For example, the person may be presented with an image of a particular surgical instrument and then asked to identify the instrument tray(s) in which the instrument may be found. The person may also be presented with an image of a particular surgical instrument and then asked to identify the type of surgical procedure in which the surgical instrument is typically used.

In still other configurations, the person may be presented with a collection of images and then asked to put the images into an order that corresponds to the order in which the surgical instruments are used when performing a particular surgical procedure.

The preceding educational activities may be directed to a person who is assisting the surgeon by providing the surgical instruments to the surgeon in the order in which the surgical instruments are utilized when performing the surgical procedure. In certain hospitals, such a person may be identified as a surgical technologist.

After being instructed on the aspects of the surgical instruments or implants, the proficiency of the person undergoing such training may be evaluated. One such test includes presenting images of a plurality of the surgical instruments or implants to the person. There may also be images of the trays in which the surgical instruments or implants are located.

Figure 8:
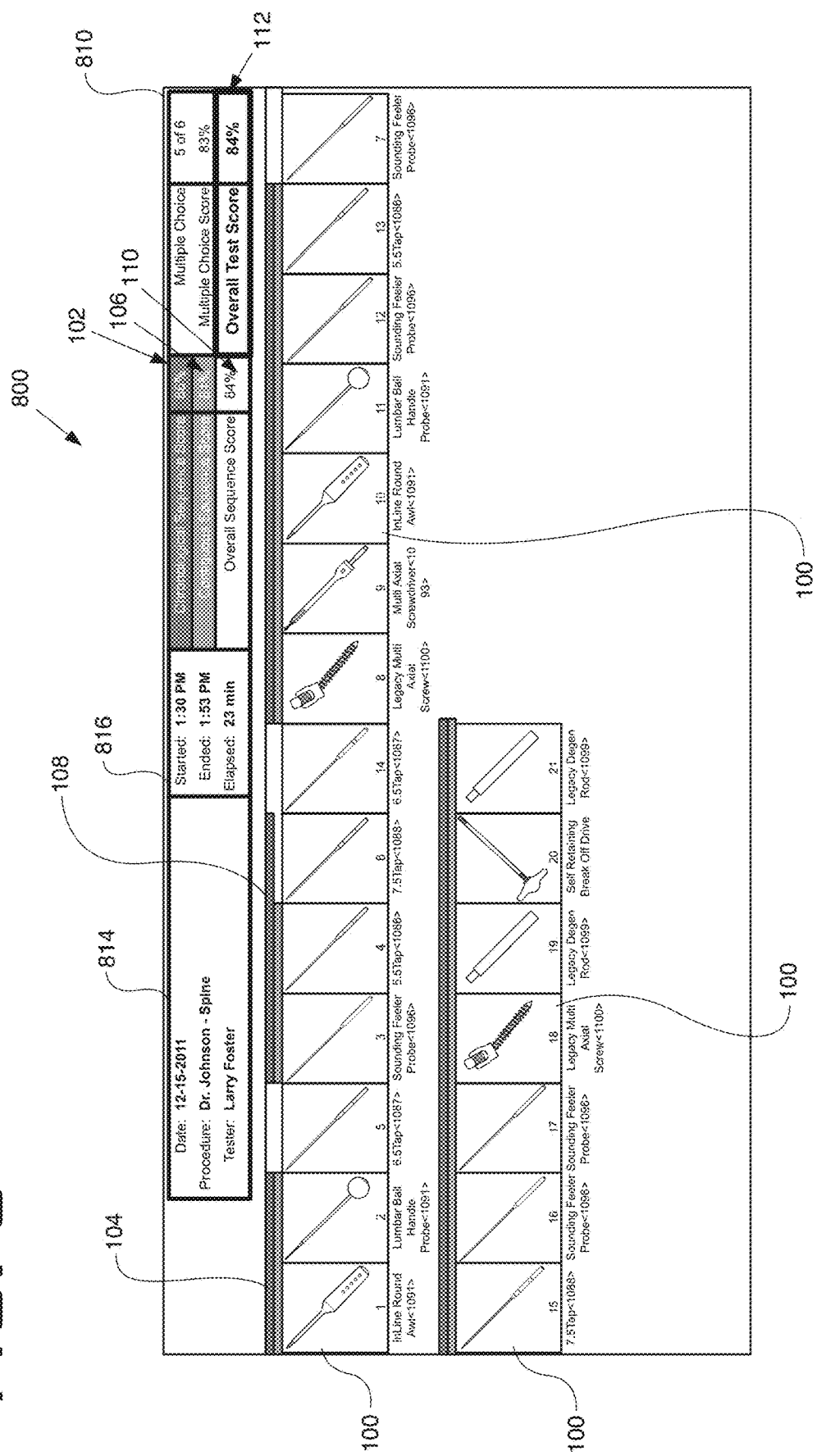
FIG. 8 is a first portion of a product training test.

The person would move the images 100 such as by dragging and dropping to the correct position that the surgical instruments or implants are used during the surgical procedure. An example of the sequence testing layout is set forth in FIG. 8.

Once the person moves the images 100 to what the person believes to be the correct location of the images 100, the person could request the sequence of images 100 to be graded such as by comparing the sequence prepared by the student to the sequence that is approved by the regulatory agency and/or the sequence that was taught to the person who is now taking the test.

The test results may be presented in more than one metric. An example of one such metric is whether the images have been placed in the correct chronological sequence. The correct chronological sequence means that the images have been placed in the correct order in which the surgical instruments or implants are supposed to be used.

In addition to providing the person with a numerical indication 102 of the number or percentage of images 100 that are in the correct chronological sequence, the system may provide a chronological sequence identifier 104 regarding the status of the images 100.

For example, the chronological sequence identifier 104 may be provided adjacent to each of the images 100 to indicate whether the associated image 100 is in the correct chronological sequence. For example, when the chronological status identifier 104 is blue may be used to indicate that the image 100 is in the correct chronological sequence. A contrasting color such as red may be used for the chronological sequence identifier 104 to indicate that the image 100 is not in the correct chronological sequence.

In one such embodiment, the chronological sequence identifier 104 may be positioned proximate an upper edge of the image. The chronological sequence identifier 104 may extend between left and right edges of the image 100. Using such a configuration provides the person with the ability to see which groups of images 100 are in the correct chronological sequence because the chronological sequence identifier 104 would extend across multiple images 100.

Another metric that may be used to evaluate the performance of the person is whether the images 100 have been placed in a correct contiguous sequence. The correct contiguous sequence means that images 100 have been correctly placed adjacent to each other. The contiguous sequence thereby assists the person to appreciate surgical instruments and implants that are used together or proximate to each other when performing the surgical procedure.

In addition to providing the person with a numerical indication 106 of the number or percentage of images 100 that are in the correct contiguous sequence, the system may provide a contiguous sequence identifier 108 regarding the status of the images 100.

For example, the contiguous sequence identifier 108 may be provided adjacent to each of the images 100 to indicate whether the associated image 100 is in the correct contiguous sequence. For example, the contiguous sequence identifier 108 may be used to indicate that the image 100 is in the correct contiguous sequence. A contrasting color such as red may be used for the contiguous sequence indicator 108 to indicate that the image 100 is not in the correct contiguous sequence.

In one such embodiment, the contiguous sequence identifier 108 may be positioned proximate an upper edge of the image 100. The contiguous sequence identifier 108 may extend between left and right edges of the image 100. Using such a configuration provides the person with the ability to see which groups of images 100 are in the correct contiguous sequence because the contiguous sequence identifier 108 would extend across multiple images 100.

While it is possible to position the chronological sequence identifier 104 in a location that is apart from the contiguous sequence identifier 104, in one such embodiment, the chronological sequence identifier 104 is placed adjacent to the contiguous sequence identifier 108. Using such a configuration enables the person to readily see which areas of the image sequence are correct.

While it is possible to provide similar weight to the correct chronological sequence and the correct contiguous sequence, in one embodiment, these metrics are assigned different weights. For example, the chronological sequence may be assigned a greater weight than the contiguous sequence such a configuration reflects the greater importance of knowing the order in which the surgical instruments or implants are used.

In one such embodiment, the chronological sequence may be assigned an importance of 60 percent and the contiguous sequence may be assigned an importance of 40 percent. After the weighting is completed, an overall sequence score 110 may be calculated.

After the grading process, the person may be provided with the opportunity to correct the positioning of the images and then have the sequence of images regraded. Similar to the initial grading process, the person may be assigned a chronological sequence score, a contiguous sequence score and an overall sequence score.

In addition to evaluating the proficiency of the person at correctly positioning the images of the surgical instruments and implants, the person may be presented with at least one additional test to measure the proficiency of the person in conjunction with the use of the surgical instruments and implants that are used in conjunction with the surgical procedure.

An example of such additional tests is a plurality of questions that require the person to select the correct answer from a list 910 of answer options. An example of one such test is 900 illustrated in FIG. 9.

The score on the additional tests may be combined with the overall sequence score 110 to provide the person with an overall test score 112. If the person attains an overall test score that is better than a threshold value, the person may be provided with a certificate that indicates the person has successfully completed the training process for the use of the surgical instruments and implants in conjunction with a particular surgical procedure.

The system may also be used in conjunction with training other persons associated with the surgical procedure. For example, educational materials may be provided for the surgeon who will be conducting the surgical procedure.

For example, when a medical device manufacturer desires to train surgeons on the techniques associated with implanting a surgical device, the medical device manufacturer may prepare an educational program that provides instruction to the surgeon on the techniques that have been approved by the regulatory organization.

Such a training program may be used in a variety of different manners. One such suitable manner is as a primary instructional guide for the surgeon. An advantage of using the system in conjunction with the training of the surgeon is that the training can be done at any time that is convenient for the person undergoing the training.

Another beneficial aspect of using the system for training is that the surgeon may periodically repeat the training. For example, if it has been an extended length of time since the surgeon has performed a particular surgical procedure, the surgeon may repeat the training.

Another way in which the system may be used is as a supplement to a live training session. Because live training sessions may only be conducted periodically, the surgeon may use the system in between when the live training sessions are offered and/or just before the surgeon performs a surgical technique that he or she does not perform on a regular basis.

A significant benefit of using the system in conjunction with educational activities is that the system can track the identity of the persons undergoing the training as well as the types of training and the length of training that were done. Such records may be used for a variety of purposes.

One such purpose is to show to a hospital that the surgical or surgical technician is sufficiently trained on aspects of a particular surgical procedure such that the surgeon or surgical technologist may be permitted to conduct or assist on the surgical procedure at the hospital.

Another way that the training records may be used is for a hospital to show that the staff at the hospital is sufficiently trained on tasks required for a particular surgical procedure so that the hospital could encourage surgeons to perform more of the surgical procedures at the hospital.

Two areas in which the surgeon may be required unique surgical procedures based upon a short-term notice include trauma and sports-related injuries. In contrast to implant procedures such as a knee or hip replacement that may be scheduled some time in advance, the trauma and sports-related injuries arise with little or no notice.

In addition to becoming more familiar on the identification of particular surgical instruments, the system may be used to increase the familiarity of aspects of product packages of implants and/or supplies that are utilized during the surgical procedure. The labels on objects such as surgical implants may be similar such that it may be challenging for a person such as the circulating nurse and/or the surgical technologist to select the correct implant.

Once the package of a surgical implant is opened, the sterility of that product can no longer be guaranteed. As such, if the package for an incorrect surgical implant is opened, that surgical implant must either be discarded or returned to the manufacturer for further processing and repackaging. Both of these aspects increase the cost of a surgical process and, as such, are desired to be avoided.

Still another manner in which the system of the invention may be used is in conjunction with correlating the aspects of a surgical procedure with the recovery of the patient. Since the system can be used to track aspects such as the amount of time that was needed to complete the surgical procedure, this data can be correlated to aspects of the patient's short-term recovery in the one to two months after the surgery. The system can also be used to correlate the length of aspects of the surgery to the patient's long-term recovery such as at 3, 6, 9 and 12 months after the surgery.

The system can also be used to compare the performances of different surgeons at conducting particular surgical procedures. For example, it could be determined that a particular surgeon typically takes 20% longer than the average to complete a surgery. Such information could be used when scheduling the usage of particular operating rooms. In situations where the patient has not approved the disclosure of data that could uniquely identify a particular patient, this information may be masked to prevent disclosure.

Yet another benefit of using the system is that it enables the surgical implants and/or surgical instrument sets to be customized to address particular needs or specialized surgical procedures because the system would guide the surgical technologist through the selection of the particular surgical implants and/or surgical instruments that are needed to perform a particular surgical technique. Examples of complex surgical procedures include total joint replacements, spinal procedures and trauma procedures.

Because the surgical instrument selection system enhances the ability to select the correct surgical instruments in a timely manner, the surgeon is more likely to select the surgical implants and associate surgical instruments from a particular manufacturer because such a system will enhance the efficiency of the operating room as opposed to surgical implants and associated surgical instrument from other manufacturers.

While it is possible for the device to further include instructions on how each of the surgical instruments may be used, such information is not needed for the surgical technologist to properly select the surgical instruments. Accordingly, instructions on the use of the surgical instruments may not be included in a typical operation mode. Rather, these types of instructions may be provided in a surgeon education mode.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing." etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A method performed by a surgical implement selection system comprising one or more computing devices, wherein the surgical implement selection system is configured to be operated in a training mode, a testing mode, and an intra-operative mode, the method comprising:
   operating the surgical implement selection system in the training mode to provide (i) information indicating an identity of each of a plurality of surgical implements, (ii) information indicating a specified location of each of the plurality of surgical implements in a surgical implement tray, and (ii) information indicating an actual order that surgical implements are used in a surgical procedure;
   providing, by the surgical implement selection system, a user interface for display on a display device, the user interface having a first display region for indicating the plurality of surgical implements and a second display region for specifying an order of the plurality of surgical implements;
   providing, by the surgical implement selection system and for display in the first display region of the user interface, images of the plurality of surgical implements;
   in response to receiving data indicating user input provided by a user to the user interface, wherein the user input indicates a user-specified order of the multiple images of the surgical implements, providing, by the surgical implement selection system, data that causes the multiple selected images to be arranged in the user-specified order in the second display region;
   evaluating, by the surgical implement selection system, whether the user-specified order of the multiple selected images matches the actual order in which the surgical implements are used when performing the surgical procedure;
   based on the evaluation, storing, by the surgical implement selection system, approval data indicating that the user of the surgical implement selection system is approved to assist with the surgical procedure;
   verifying, by the surgical implement selection system, an identity of the user;
   in response to verifying the identity of the user and the user having associated approval data indicating that the user is approved to assist with the surgical procedure, providing, by the surgical implement selection system, the user access to the surgical implement selection system during a surgery to perform the surgical procedure, wherein the surgical implement selection system is configured to restrict access to the surgical implement selection system during the surgical procedure for users not having associated approval data indicating approval to assist with the surgical procedure; and
   after providing the user access to the surgical implement selection system during a surgery to perform the surgical procedure, operating the surgical implement selection system in the intra-operative mode to track use of one or more of the surgical implements during the surgery, wherein tracking the use of the one or more surgical implements comprises detecting use of the one or more surgical implements using the one or more scanning devices configured to detect surgical implements used during the surgery.

2. The method of claim 1, wherein providing the images of the plurality of surgical implements comprises providing, by the surgical implement selection system and for display in the first display region of the user interface, an image of a surgical implement tray with the images of the plurality of surgical implements.

3. The method of claim 1, wherein the images of the plurality of surgical implements comprise an image of at least one surgical instrument.

4. The method of claim 1, wherein the images of the surgical implements comprise an image of at least one surgical implant.

5. The method of claim 1, further comprising providing a comment or annotation with the information indicating the identity of the plurality of surgical implements, the specified locations, or the actual order.

6. The method of claim 1, wherein providing information indicating the identity of the plurality of surgical implements, providing information indicating the specified location of each of the plurality of surgical implements, and providing information indicating the actual order each comprise displaying a video by the surgical implement selection system, outputting audio by the surgical implement selection system, or displaying manipulatable images of the surgical implements by the surgical implement selection system.

7. The method of claim 1, wherein the actual order is an order of the surgical implements that is customized for a particular surgeon.

8. The method of claim 1, further comprising providing, by the surgical implement selection system, a user interface for defining a custom template that indicates customized parameters for a surgical procedure; and storing the custom template at the surgical implement selection system.

9. The method of claim 1, further comprising providing, by the surgical implement selection system, an indication of which of the selected images in the second display region are arranged in a correct sequence and which of the selected images in the second display region are arranged in an incorrect sequence.

10. The method of claim 1, further comprising providing, by the surgical implement selection system, an indication of a subset of the selected images in the second display region that are arranged in a correct contiguous sequence.

11. The method of claim 1, wherein evaluating whether the user-specified order of the multiple selected images matches the actual order in which the surgical implements are used when performing the surgical procedure comprises:
   in response to user input indicating that the user-specified order is complete, determining, by the surgical implement selection system, an amount of the multiple selected images in the user-specified order that match the actual order;

wherein the method further comprises providing, by the surgical implement selection system, and for display on the user interface, a metric indicating the amount of the multiple selected images in the user-specified order that match the actual order.

12. The method of claim 1, wherein the surgical implement selection system comprises a server, and wherein providing the user interface for display on a display device comprises providing, by the server, data for the user interface over a computer network to a client device that includes the display device.

13. The method of claim 1, wherein providing images of the plurality of surgical implements comprises: providing, for display in the first display region, the images of the plurality of surgical implements and the image of a surgical implement tray with the images of the plurality of surgical implements being arranged according to their specified locations in the surgical implement tray; and wherein providing the data that causes the multiple selected images to be arranged in the user-specified order in the second display region comprises: displaying the selected images of the surgical implements in the second display region in response to receiving first user input that selects images of the surgical implements from the specified locations that the images of the surgical implements are shown in the first display region with respect to the image of the surgical implement tray.

14. The method of claim 1, further comprising:
determining, by the surgical implement selection system, that a particular surgical implement has not been used during the surgery based on the detection of use of the one or more surgical implements using the one or more scanning devices; and
providing, by the surgical implement selection system, an alert during the surgery based on determining that the particular surgical implement has not been used during the surgery.

15. The method of claim 1, wherein operating the surgical implement selection system in the intra-operative mode to track use of one or more of the surgical implements during the surgery comprises detecting use of one or more of the surgical implements using a bar code reader of the surgical implement selection system or an RFID tag reader of the surgical implement selection system.

16. A method performed by a surgical implement selection system comprising one or more computing devices, wherein the surgical implement selection system is configured to be operated in a training mode, a testing mode, and an inter-operative mode, the method comprising:
operating the surgical implement selection system in the training mode to provide (i) information indicating an identity of each of a plurality of surgical implements, (ii) information indicating a specified location of each of the plurality of surgical implements in a surgical implement tray, and (ii) information indicating an actual order that surgical implements are used in a surgical procedure;
providing, by the surgical implement selection system, a user interface for display on a display device, the user interface having a first display region for indicating the plurality of surgical implements and a second display region for specifying an order of the plurality of surgical implements;
providing, by the surgical implement selection system and for display in the first display region of the user interface, an image of a surgical implement tray and images of the plurality of surgical implements;
in response to the surgical implement selection system receiving first user input that selects multiple images of the surgical implements in the first display portion, providing the selected images of the surgical implements for display in the second display region of the user interface;
in response to the surgical implement selection system receiving data indicating second user input that interacts with the selected images in the second display region and indicates a user-specified order of the selected images, providing, by the surgical implement selection system, data that causes the multiple selected images to be arranged in the user-specified order in the second display region;
evaluating, by the surgical implement selection system, whether the user-specified order of the multiple selected images matches the actual order in which the surgical implements are used when performing the surgical procedure;
based on the evaluation, storing, by the surgical implement selection system, approval data indicating that the user of the surgical implement selection system is approved to assist with the surgical procedure;
verifying, by the surgical implement selection system, an identity of the user;
in response to verifying the identity of the user and the user having associated approval data indicating that the user is approved to assist with the surgical procedure, providing, by the surgical implement selection system, the user access to the surgical implement selection system during a surgery to perform the surgical procedure, wherein the surgical implement selection system is configured to restrict access to the surgical implement selection system during the surgical procedure for users not having associated approval data indicating approval to assist with the surgical procedure; and
after providing the user access to the surgical implement selection system during a surgery to perform the surgical procedure, operating the surgical implement selection system in the intra-operative mode to track use of one or more of the surgical implements during the surgery, wherein tracking the use of the one or more surgical implements comprises detecting use of the one or more surgical implements using the one or more scanning devices configured to detect surgical implements used during the surgery.

17. The method of claim 16, further comprising:
providing, by the surgical implement selection system, an image of a particular surgical implement;
receiving, by the surgical implement selection system, data indicating user input specifying a user-indicated surgical procedure corresponding to the particular surgical implement;
determining, by the surgical implement selection system, that the user-indicated surgical procedure matches an actual surgical procedure that the particular surgical implement is used to perform;
wherein storing the data indicating that the user of the surgical implement selection system is approved to assist with the surgical procedure is further based on determining that the user-indicated surgical procedure matches the actual surgical procedure that the particular surgical implement is used to perform.

18. A method performed by a surgical implement selection system comprising one or more computing devices, wherein the surgical implement selection system is configured to be operated in a training mode, a testing mode, and an inter-operative mode, the method comprising:

operating the surgical implement selection system in the training mode to provide (i) information indicating an identity of each of a plurality of surgical implements, (ii) information indicating a specified location of each of the plurality of surgical implements in a surgical implement tray, and (ii) information indicating an actual order that surgical implements are used in a surgical procedure;

providing, by the surgical implement selection system, a user interface for display on a display device, the user interface having a first display region for indicating the plurality of surgical implements and a second display region for specifying an order of the plurality of surgical implements, wherein the surgical implement selection system comprises a server, and wherein providing the user interface comprises providing the data for the user interface over a computer network to a client device that includes the display device;

providing, by the surgical implement selection system and for display in the first display region of the user interface, images of the plurality of surgical implements;

in response to receiving data indicating user input provided by a user to the user interface, wherein the user input indicates a user-specified order of the multiple images of the surgical implements, providing, by the surgical implement selection system, data that causes the multiple selected images to be arranged in the user-specified order in the second display region;

evaluating, by the surgical implement selection system, whether the user-specified order of the multiple selected images matches the actual order in which the surgical implements are used when performing the surgical procedure;

based on the evaluation, storing, by the surgical implement selection system, approval data indicating that the user of the surgical implement selection system is approved to assist with the surgical procedure;

verifying, by the surgical implement selection system, an identity of the user;

in response to verifying the identity of the user and the user having associated approval data indicating that the user is approved to assist with the surgical procedure, providing, by the surgical implement selection system, the user access to the surgical implement selection system during a surgery to perform the surgical procedure, wherein the surgical implement selection system is configured to restrict access to the surgical implement selection system during the surgical procedure for users not having associated approval data indicating approval to assist with the surgical procedure; and after providing the user access to the surgical implement selection system during a surgery to perform the surgical procedure, operating the surgical implement selection system in the intra-operative mode to track use of one or more of the surgical implements during the surgery, wherein tracking the use of the one or more surgical implements comprises detecting use of the one or more surgical implements using the one or more scanning devices configured to detect surgical implements used during the surgery.

* * * * *